United States Patent

Itakura et al.

[11] Patent Number: 6,165,615
[45] Date of Patent: Dec. 26, 2000

[54] GRADUAL-RELEASING CAPSULE AND METHOD FOR MANUFACTURING THE SAME

[75] Inventors: Keisuke Itakura; Misao Yagi, both of Hiratsuka, Japan

[73] Assignee: Takasago International Corporation, Tokyo, Japan

[21] Appl. No.: 09/124,793

[22] Filed: Jul. 30, 1998

[30] Foreign Application Priority Data

Jul. 30, 1997  [JP]  Japan .................................. 9-204649

[51] Int. Cl.⁷ ...................................................... B32B 5/16
[52] U.S. Cl. ........................................................ 428/407
[58] Field of Search .......................... 428/402.2, 402.21, 428/403, 407

[56] References Cited

U.S. PATENT DOCUMENTS

| | | | |
|---|---|---|---|
| 3,870,542 | 3/1975 | Ida et al. ................................. | 117/33.3 |
| 3,872,023 | 3/1975 | Baum et al. ............................. | 252/316 |
| 4,428,869 | 1/1984 | Munteau et al. ........................ | 252/522 A |
| 5,204,121 | 4/1993 | Bucheler et al. ....................... | 424/495 |
| 5,512,753 | 4/1996 | Thomson et al. ....................... | 250/361 R |
| 5,770,222 | 6/1998 | Unger et al. ............................. | 424/450 |

FOREIGN PATENT DOCUMENTS

| | | |
|---|---|---|
| 3718934 | 12/1987 | Germany . |
| 62-180744 | 8/1987 | Japan . |
| 02000205 | 1/1990 | Japan . |
| 02113860 | 4/1990 | Japan . |
| 09155183 | 6/1997 | Japan . |
| 11047581 | 2/1999 | Japan . |
| 2192171 | 12/1987 | United Kingdom . |

*Primary Examiner*—H. Thi Le
*Attorney, Agent, or Firm*—Kubovcik & Kubovcik

[57] ABSTRACT

A gradual releasing capsule having large mechanical strength, a large grain size and excellent gradual-releasability and its production method are disclosed. The capsule comprises a polymer core body containing a hydrophobic oil and a shell body formed of a cured body with which the surface of the core body is covered. The capsule is produced by dripping a core body-forming composition containing a hydrophobic oil and a reactive monomer and a curable polymer-containing solution from a multiple nozzle into a coagulating solution to form a primary capsule and then polymerizing the reactive monomer in the primary capsule.

22 Claims, 1 Drawing Sheet

GRADUAL-RELEASING CAPSULE AND METHOD FOR MANUFACTURING THE SAME

BACKGROUND OF THE INVENTION

1. Field of the invention

This invention relates to a gradual-releasing, i.e., sustained release, capsule containing a hydrophobic oil in the core and to a method for manufacturing the same.

2. Description of the Related Art

A capsule having a uniform grain size and which contains, in a curable polymer, a hydrophobic oil which is introduced using a multiple nozzle, e.g. a double nozzle, triple nozzle, and its production method called "insolubilizing method" (or a nozzle method) have been known for long. The production of a capsule by the insolubilizing method is described, for example, in the reference "Microcapsule" edited by Tamotsu Kondo, Japan Standards Association, p. 248, and in Japanese Patent Application Laid-Open (JP-A) Nos. S44-11914 and H65-9178.

A method called "in situ polymerization method" is known in which a mixture consisting of a reactive monomer, hydrophobic oil, and polymerization initiator is dispersed in water using a surfactant and this emulsion solution is heated or irradiated with light to polymerize the reactive monomer in the emulsion thereby producing a capsule. This method is also described, for example, in the reference "Microcapsule" edited by Tamotsu Kondo, Japan Standards Association, p. 24.

The insolubilizing method makes it possible to prepare a uniform capsule with a relatively large grain size of 0.5 to 5 mm. The in situ polymerization method yields a microcapsule with a grain size of several micrometers to tens of micrometers and is therefore applied to carbonless paper or the like.

The preparation of a multiple capsule which has a relatively large and uniform grain size, contains a hydrophobic oil therein, and is strong and superior in gradual-releasability is, however, difficult as in the past.

SUMMARY OF THE INVENTION

An object of the present invention is to provide a capsule which has a uniform grain size and can gradually release the fragrance of an encapsulated hydrophobic oil and also to provide a method for manufacturing such a capsule.

Another object of the present invention is to provide a capsule which has a relatively large and uniform grain size of 1 to 5 mm, a relatively large breaking strength of 100 to 5,000 g/cm and is strong and superior in gradual-releasability and also to provide a method for manufacturing such a capsule.

According to a first aspect of the present invention, there is provided a gradual-releasing capsule comprising:
a core body composed of a polymer containing a hydrophobic oil; and
a shell body with which the core body is coated and which is composed of the cured product of a curable polymer.

In a preferred embodiment of the gradual-releasing capsule of the present invention, the core body is produced by polymerizing a reactive monomer contained in a core body-forming composition which includes the hydrophobic oil and the reactive monomer. The core body-forming composition may contain polymerization initiators or diluents, if necessary.

In a preferred embodiment of the gradual-releasing capsule of the present invention, the reactive monomer is at least one compound selected from the group consisting of acrylates, methacrylates, acrylic acid amides, methacrylic acid amides, isocyanates, vinyl chloride, styrene or its derivatives, and divinylbenzene or its derivatives.

In a preferred embodiment of the gradual-releasing capsule of the present invention, the shell body is produced by curing the curable polymer contained in a solution containing a natural curable polymer and/or a synthetic curable polymer.

In a preferred embodiment of the gradual-releasing capsule of the present invention, the curable polymer is a cool-curable polymer which is cured by cooling and/or a salt-curable polymer which is cured by a salt.

According to another aspect of the present invention, there is provided a method for manufacturing a gradual-releasing capsule comprising:
forming a primary capsule in which a liquid droplet of a core body-forming composition containing a hydrophobic oil and a reactive monomer is coated with the cured product of a natural curable polymer and/or a synthetic curable polymer; and
polymerizing the reactive monomer.

According to a further aspect of the present invention, there is provided a method for manufacturing a gradual-releasing capsule comprising:
forming a primary capsule in which a liquid droplet of a core body-forming composition containing a hydrophobic oil and a reactive monomer is coated with a shell body formed of the cured product of a natural curable polymer and/or a synthetic curable polymer; and
polymerizing the reactive monomer to form a secondary capsule; and
introducing the secondary capsule into an aqueous alkali to remove or weaken the shell body.

DESCRIPTION OF THE PREFERRED EMBODIMENTS

A. Gradual-releasing capsule

1. Core body

Figure 1:
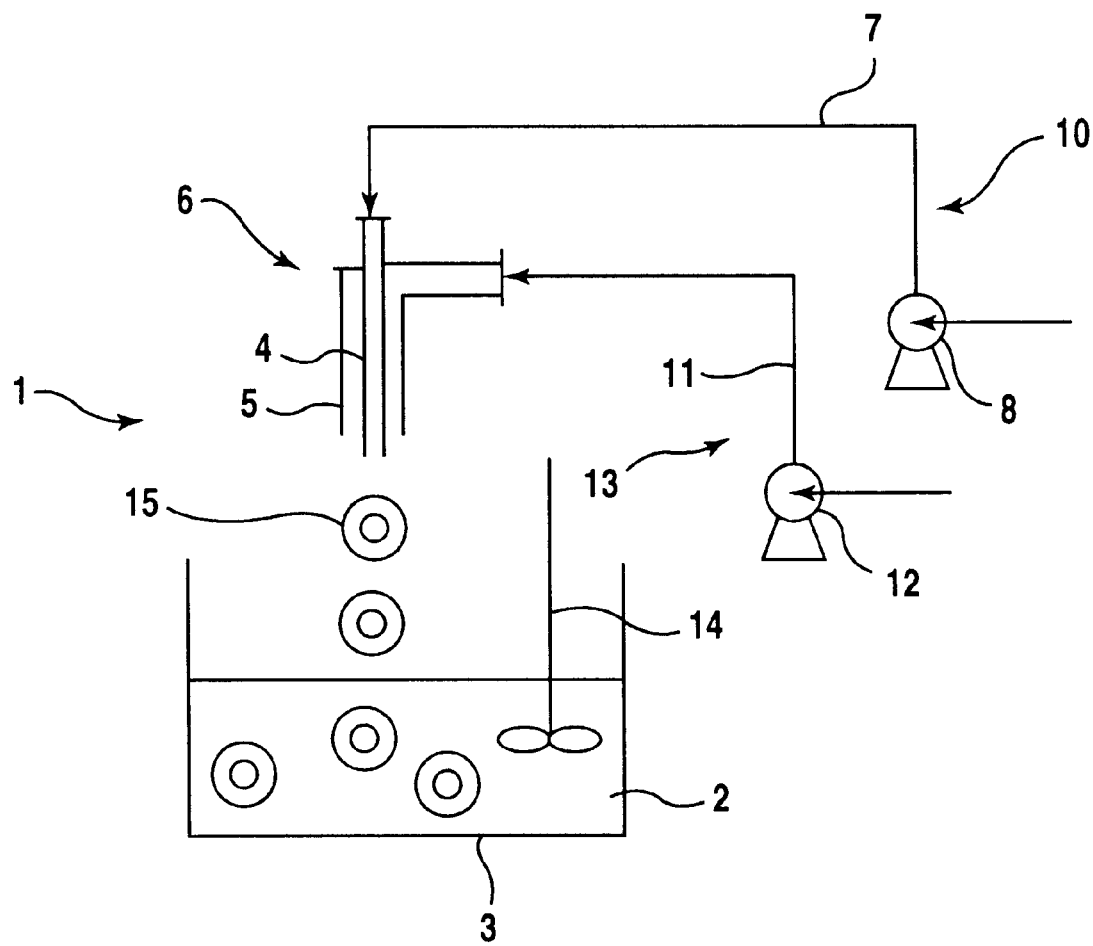
FIG. 1 is a conceptional view showing an apparatus for manufacturing a primary capsule of an embodiment of the present invention.

The gradual-releasing capsule comprises a core body and a shell body encapsulating the core body.

The core body is composed of a polymer containing a hydrophobic oil. The hydrophobic oil is in such a condition that the polymer is impregnated with the hydrophobic oil.

Here, the hydrophobic oil means an oil which is slightly soluble in water. As this hydrophobic oil, perfumes which are useful as a fragrance and are slightly soluble in water can be exemplified. Examples of such perfumes include animal perfumes such as a musk oil, vegetable perfumes such as ambut seed oil, ylang yalang oil, oakmoss oil, opopanax oil, and rose oil, synthetic perfumes such as linalool, linalyl acetate, menthol, hedion, lemon terpene, orange terpene, spearmint oil, peppermint oil, lime oil, eugenol, citronellol, musk ketone, and mixed perfumes containing these. The hydrophobic oil may be an oil having a medical effect, such as a drug.

The polymer may be impregnated with this hydrophobic oil which is diluted in a diluent including a high boilingpoint solvent such as a fatty acid ester of glycerol or benzyl benzoate. When the hydrophobic oil is diluted in a diluent, its gradual-releasability from the gradual-releasing capsule can be controlled according to the desired dilution. In the case of using such a diluent, the diluent is used in an amount of 100 to 1,000 parts by weight and preferably 100 to 500 parts by weight for 100 parts by weight of the hydrophobic oil.

The above polymer is, for example, a polymer obtained by polymerizing a reactive monomer. As the reactive monomer, monomers which can be polymerized by a radical polymerization method or other polymerization methods may be used. A desirable reactive monomer used in the present invention is an olefin-type monomer which can be polymerized by the aid of a radical or light radiation-polymerization initiator. Examples of the olefin-type monomer include acrylates, methacrylates, acrylic acids, methacrylic acids, styrene and its derivatives, vinyl chloride, diisocyanates, and divinylbenzene.

More specifically, preferable examples of the reactive monomer include acrylic acid, methacrylic acid, methylacrylate, ethylacrylate, tetraethylene glycol diacrylate, methylmethacrylate, ethylmethacrylate, tetraethylene glycol dimethacrylate, styrene, α-methylstyrene, vinyl chloride, ethylene diisocyanate, hexamethylene diisocyanate, and divinylbenzene.

In the present invention, a preferable reactive monomer is a combination of a monofunctional monomer such as styrene and a polyfunctional monomer such as divinylbenzene and, more specifically, a combination of styrene or its derivative and divinylbenzene or a combination of methacrylates or methacrylic acids and divinylbenzene.

When a monomer having a so-called unsaturated double bond among the above reactive monomers is polymerized, a polymerization initiator is allowed to coexist. When diisocyanates are polymerized, in turn, a desirable effect can be obtained if a solidification agent is allowed to coexist. Examples of such a solidification agent include diols such as ethylene glycol and propylene glycol and diamines such as ethylenediamine, propylenediamine.

As examples of the polymerization initiator, peroxides such as benzoyl peroxide and azobisisobutyronitrile and redox-type catalysts such as $Fe^{++}$—$H_2O_2$ are given.

Preferably the amount of the polymerization initiator which is allowed to coexist with the reactive monomer is 0.01 to 0.5 parts by weight for 100 parts by weight of the reactive monomer.

The reactive monomer can be polymerized at 40 to 80° C. for 30 minutes to 24 hours.

The core body in the present invention contains the hydrophobic oil in an amount of 1 to 300 parts by weight and preferably 10 to 200 parts by weight for 100 parts by weight of the polymer.

In the present invention, the diameter of the core body is generally 0.5 to 3 mm.

2. Shell body

The shell body in the present invention is formed of at least one coating layer composed of a cured body of a curable polymer applied to the surface of the core body. This cured body may be configurationally designated as "a solidified body" since the curable polymer which has been soft or fluid until that time is solidified or may be called "a gelled solid substance" when viewed from another angle since the curable polymer is gelled and cured or solidified. Examples of the curable polymer include cool-curable polymers and salt-curable polymers.

The cool-curable polymer is a polymer which is gelled and cured or solidified when it is cooled. As typical examples of the cool-curable polymer, natural polymers such as gelatin and agar are known. One or more polyhydric alcohols such as sorbitol or glycerol may be added to the natural polymer.

The above salt-curable polymer is a polymer which is gelled and cured or solidified by a salt. Given as typical examples of the salt are natural polymers such as sodium alginate, pectin, carageenan, carboxymethyl cellulose, and gelant gum, and synthetic polymers obtained from monomers such as sodium acrylate and sodium methacrylate.

The cured body in the present invention may be a treated cured body produced by further treating the cured bodies of the above cool-curable polymer and salt-curable body.

This treated cured body can be prepared by crosslinking and thereby curing, in the presence of a crosslinking agent such as glutaraldehyde, the cured body produced by curing, for example, the cool-curable polymer. The use of the treated cured body produced by the crosslinking and curing operation contributes to a further improvement in the strength of the shell body.

Though the shell body may be formed of one coating layer composed of the cured body of the above one or more types of curable polymer, it maybe formed of a plurality of coating layers composed of different cured bodies of different curable polymers as required.

The entire thickness of the shell body of the gradual-releasing capsule in the present invention is generally 0.5 to 3 mm.

3. Characteristics of the gradual-releasing capsule

In general the gradual-releasing capsule according to the present invention has a diameter of 1 to 5 mm which is almost the same as that of a capsule produced by an insolubilizing method.

This gradual-releasing capsule has a core body containing the polymer impregnated with the hydrophobic oil having fragrance and the surface of the core body is coated with the cured polymer (that is, the solidified body or gelled solid substance). The breaking strength reaches even up to 100 to 5,000 g/cm². In this gradual-releasing capsule, the hydrophobic oil contained in the inside of the gradual-releasing capsule is gradually released via the cured body.

If the gradual-releasing capsule is dipped in an aqueous alkali such as caustic soda or sodium carbonate when the shell body is composed of the cured body of the salt-curable polymer, the shell body can be easily broken by external pressure thereby promoting the gradual-releasability.

B. Method for producing the gradual-releasing capsule

The gradual-releasing capsule according to the present invention can be manufactured by the production method of the invention. The method for manufacturing the gradual-releasing capsule of the present invention comprises forming a primary capsule in which a liquid droplet of a core body-forming composition containing a hydrophobic oil and a reactive monomer is coated with the cured product of a natural curable polymer and/or a synthetic curable polymer, and polymerizing the reactive monomer.

1. Formation of the primary capsule

The primary capsule can be formed by dripping (1) a liquid core body-forming composition containing a hydrophobic oil, a reactive monomer, a polymerization initiator, and a diluent to be formulated as required and (2) a curable polymer-containing solution including a natural curable polymer and/or a synthetic curable polymer into a coagulating solution from a multiple nozzle.

The hydrophobic oil, reactive monomer, polymerization initiator, diluent, natural curable polymer, and synthetic curable polymer are as described above.

The curable polymer-containing solution may include either the natural curable polymer or the synthetic curable polymer or a mixture of these and may be diluted with an appropriate solvent.

For the multiple nozzle, in the case of producing a gradual-releasing capsule comprising a core body and a one-layer shell body applied to the core body, a double nozzle is adopted and in the case of producing a gradual-releasing capsule comprising a core body and a two-layer shell body applied to the core body, a triple nozzle is adopted.

In the formation of the primary capsule, the core body-forming composition is dripped from a so-called center nozzle used in the formation of a multiple component capsule and the curable polymer-containing solution is dripped from a circular nozzle surrounding the center nozzle. The double nozzle may have an end formed with an inner cylinder and an outer cylinder which is concentric with the inner cylinder. Since the core body-forming composition is dripped from the inner cylinder of the nozzle, it is called an "inner cylinder solution". Also, since the curable polymer-containing solution is dripped from a circular opening formed between the inner cylinder and the outer cylinder, it is called an "outer cylinder solution".

When the double nozzle is used, the outer diameter of the inner cylinder is designed to be in a range from 0.4 to 2 mm and preferably from 0.5 to 1.5 mm and the outer diameter of the outer cylinder is designed to be in a range from 0.8 to 3 mm and preferably from 1 to 2.5 mm. A double nozzle having such a dimension makes it possible to form a gradual-releasing capsule having a diameter of 1 to 5 mm with ease.

As the coagulating solution, a cooled liquid paraffin, vegetable oil, or the like may be used when the curable polymer in the solution containing the curable polymer is a cool-curable polymer. As the cooling temperature at this time, a temperature lower than the gelling point of the curable polymer in the solution containing the curable polymer is appropriately selected.

When the curable polymer is a salt-curable polymer, in turn, an aqueous solution containing a curable salt including a calcium salt such as calcium chloride, calcium lactate and calcium phosphate or a potassium salt such as potassium chloride and potassium phosphate can be used as the coagulating solution. The type of curable salt to be adopted is appropriately selected according to a particular combination with the salt-curable polymer. Preferably the curable salt is used in an amount of 5 to 50 parts by weight for 100 parts by weight of the salt-curable polymer though the amount of the curable salt may be greatly in excess of the amount of the salt-curable polymer. In the process of manufacturing the gradual-releasing capsule, the temperature of a coagulating solution as the solution of the curable salt is generally 0 to 15° C.

FIG. 1 shows a conceptional view of an apparatus for manufacturing the primary capsule using a double nozzle as the multiple nozzle.

As shown in FIG. 1, an apparatus 1 for manufacturing the primary capsule comprises a container 3 containing a coagulating solution 2, a double nozzle 6 which is opened downward and has inner and outer cylinders 4,5 and is disposed above the container 3, an inner cylinder solution supplying means 10 including a pipe 7 and a feed pump 8 for supplying an inner cylinder solution to the inner cylinder 4 of the double nozzle 6, and an outer cylinder solution supplying means 13 including a pipe 11 and a feed pump 12 for supplying an outer cylinder solution to a circular outer nozzle formed between the inner cylinder 4 and outer cylinder of the double nozzle 6. The symbol 14 represents a stirring means for agitating the coagulation solution 2 and the symbol 15 represents a droplet.

In such an apparatus 1 for manufacturing the primary capsule, the inner cylinder solution (liquid core body-forming composition) and the outer cylinder solution (curable polymer-containing solution) are dripped simultaneously from the center nozzle and outer nozzle of the double nozzle 6, respectively. The droplet that is dripped falls down into the coagulating solution 2 and the curable polymer in the outer cylinder solution is cured by the coagulating solution 2.

When the curable polymer is the cool-curable polymer, it is clear that the curable polymer in the curable polymer-containing solution contained in a droplet dripped from the double nozzle starts to cure while the droplet falls in the air from the double nozzle into the coagulating solution because the double nozzle is positioned above the coagulating solution. In order for the cured body of the curable polymer in the droplet falling in the air to be kept as spherical as possible, some means for attaining the formation of a spherical cured body of the curable polymer is desired. For example, the droplet may be rotated by some means.

As a consequence, a primary capsule is formed which comprises a spherical shell body and a core body-forming composition which is maintained as a liquid in the shell body.

The double nozzle is disposed above the coagulating solution, but may be designed to be dipped into the coagulating solution. In this case, when the curable polymer-containing solution containing the salt-curable polymer is used, the primary capsule can be formed, for example, according to a method described in Japanese Patent Application Laid-Open (JP-A) No. S49-59789, which is incorporated herein by reference.

2. Formation of the gradual-releasing capsule

After the primary capsule is formed, for example, the primary capsules which are present in the coagulating solution contained in the container are collected. The collected primary capsule is then subjected to polymerization of the core body-forming composition. Specifically, the reactive monomer in the core body-forming solution encapsulated within the shell body of the primary capsule is polymerized.

The polymerization is performed under general polymerization conditions according to the type of reactive monomer. In a preferred condition, heating is carried out at 40 to 80° C. for 2 to 6 hours. It is desirable to heat the coagulating solution itself in which the primary capsule exists. In a method of heating the coagulating solution itself, because it is not necessary to collect the primary capsules in the coagulating solution, to introduce the collected capsules into a heater, or to heat at a prescribed temperature, the method is simplified to that extent.

Completion of the polymerization yields a gradual-releasing capsule comprising a polymer impregnated with the hydrophobic oil encapsulated in the shell body.

After the completion of the polymerization, the gradual-releasing capsules are collected and washed, followed by drying such as by through-flow drying, fluidized drying, or freeze drying.

Because the gradual-releasing capsule prepared in this manner has a shell body with a large mechanical strength and a core body that is polymerized and solidified, it has large mechanical strength and is characterized in that a hydrophobic oil with which the core body is impregnated is gradually released. Unreacted curable polymer contained in the shell body can be further cured by heating the resulting capsule to improve the mechanical strength. The mechanical strength and gradual-releasability of the capsule can be controlled by selecting the type, concentration, and composition of the reactive monomer in the core body forming composition and the type, concentration, and composition of the curable polymer in the curable polymer-containing solution. The gradual-releasability, when the shell body is the cured body of a salt-curable polymer, can also be controlled by introducing the capsule into an aqueous alkali to weaken the cured body and by applying external pressure onto the capsule by any means to break a part or all of the shell body.

According to the present invention, a gradual-releasing capsule having large mechanical strength, a large grain size, and excellent gradual-releasability is provided. A simple method for producing the gradual-releasing capsule is also provided.

Particularly, in the production method of the present invention, the gradual-releasability of the capsule can be controlled with ease.

The capsule is characterized in that it has a relatively large grain size (0.5 to 5 mmø), a large breaking strength (100 to 5,000 kg/cm$^2$), and an appropriate gradual-releasability. The capsule can be applied in industrial fields, for example, in cases where a perfume is used as the hydrophobic oil, and to fragrances and candles.

EXAMPLES

The present invention will be illustrated in more detail by way of examples, which are not intended to limit of the present invention.

Example 1

The following inner and outer cylinder solutions were prepared and continuously supplied using a fixed delivery pump to form droplets continuously from a double nozzle in an apparatus for manufacturing a capsule as shown in FIG. 1. The droplets were cured by discharging them into the curing solution (coagulating solution) to form a primary capsule.

Outline of the manufacturing apparatus:
  Diameter of inner cylinder: 0.8 mm
  Diameter of outer cylinder: 2 mm
Composition of inner cylinder solution:

| | |
|---|---|
| Perfume (Trademark: ON-CIFL-204-E citrus base, manufactured by Takasago Corporation) | 2.5 g |
| Fatty acid ester of glycerol | 2.5 g |
| Styrene | 3.8 g |
| Divinylbenzene | 0.9 g |
| Azoisobutyronitrile | 0.05 g |

Temperature of the inner cylinder solution: 25° C.
Outer cylinder solution;
  2% sodium alginate (Trade mark: I-1, manufactured by Kimitsu Chemical Co., Ltd.) 5 g
Temperature of the outer cylinder solution: 25° C.
Coagulating solution;
  Type: aqueous 10% calcium chloride solution
  Liquid temperature: 5° C.
Dripping rates of the inner and outer cylinder solutions: 0.5 cc/second Following formation of the primary capsules, the aqueous curing solution was heated at 60° C. with stirring for two hours to polymerize the styrene and divinylbenzene. The resulting secondary capsule was washed and then dried to obtain a gradual-releasing capsule having a core body and a shell body formed of one layer.

The breaking strength of the gradual-releasing capsule which was measured using a rheometer (Trademark: NRM-2010 J-CW, manufactured by Fudo) was 390 g/cm$^2$. The capsule maintained its fragrance peculiar to the perfume even after it was allowed to stand for over one month.

Example 2

A capsule was produced in the same manner as in Example 1 except that the composition of the inner cylinder solution was altered to that described below. The breaking strength of the gradual-releasing capsule which was measured in the same manner as in Example 1 was 4,800 g/cm$^2$. The capsule maintained its fragrance peculiar to the perfume even after it was allowed to stand for over two months.
Composition of inner cylinder solution:

| | |
|---|---|
| Perfume (the same as in Example 1, manufactured by Takasago Corporation) | 1.5 g |
| Fatty acid ester of glycerol | 1.5 g |
| Styrene | 1 g |
| Divinylbenzene | 10 g |
| Azoisobutyronitrile | 0.5 g |

Temperature of the inner cylinder solution: 25° C.

Example 3

A capsule was produced in the same manner as in Example 1 except that the composition of the inner cylinder solution was altered to that described below. The breaking strength of the gradual-releasing capsule which was measured in the same manner as in Example 1 was 4,600 g/cm$^2$. The capsule maintained its fragrance peculiar to the perfume even after it was allowed to stand for over one month.
Composition of inner cylinder solution:

| | |
|---|---|
| Perfume (the same as in Example 1, manufactured by Takasago Corporation) | 5 g |
| Methylmethacrylate | 8 g |
| Methacrylic acid | 0.5 g |
| Divinylbenzene | 2 g |
| Azoisobutyronitrile | 0.5 g |

Temperature of the inner cylinder solution: 25° C.

Example 4

A capsule was produced in the same manner as in Example 1 except that the compositions of the outer cylinder solution and the curable solution were altered to those described below. The resulting capsule was collected and was introduced into an aqueous 2% glutaraldehyde solution, followed by stirring at room temperature for 12 hours to insolubilize a gelatin and then heated at 60° C. for two hours to produce a double layer capsule.

The breaking strength of the gradual-releasing capsule which was measured in the same manner as in Example 1 was 400 g/cm$^2$. The capsule maintained its fragrance peculiar to the perfume even after it was allowed to stand for over one month.

Outer cylinder solution: aqueous 5% gelatin solution
Curing solution: cooled liquid paraffin (0° C.)

Example 5

The capsule obtained in Example 2 was dipped in an aqueous 10% caustic soda overnight. After the resulting capsule was washed, the shell body of the capsule was crushed using a mill, classified using a filter, and subjected to through-flow drying to obtain a capsule having a breaking strength of 4,800 g/cm$^2$. The capsule maintained its fragrance peculiar to the perfume even after it was allowed to stand for over one month.

What is claimed is :

1. A gradual-releasing capsule comprising a core body formed of a polymer containing a hydrophobic oil and a shell body formed of a cured body of a curable polymer, the core body being coated with the shell body.

2. A gradual-releasing capsule according to claim 1, wherein said core body is produced by polymerizing a reactive monomer contained in a core body-forming composition including the hydrophobic oil and the reactive monomer.

3. A gradual-releasing capsule according to claim 2, wherein said core body-forming composition contains the hydrophobic oil, the reactive monomer, a polymerization initiator and/or a diluent.

4. A gradual-releasing capsule according to claim 2, wherein said reactive monomer is at least one compound selected from the group consisting of acrylic acids, methacrylic acids, acrylates, methacrylates, acrylic acid amides, methacrylic acid amides, isocyanates, vinyl chloride, styrene or its derivatives, and divinylbenzene or its derivatives.

5. A gradual-releasing capsule according to claim 2, wherein said shell body is produced by curing the curable polymer which is contained in an aqueous solution containing a natural curable polymer and/or a synthetic curable polymer.

6. A gradual-releasing capsule according to claim 5, wherein said curable polymer is a cool-curable polymer which is cured by cooling and/or a salt-curable polymer which is cured by a salt.

7. A gradual-releasing capsule according to claim 1, wherein said shell body is produced by curing the curable polymer which is contained in an aqueous solution containing a natural curable polymer and/or a synthetic curable polymer.

8. A gradual-releasing capsule according to claim 7, wherein said curable polymer is a cool-curable polymer which is cured by cooling and/or a salt-curable polymer which is cured by a salt.

9. A gradual-releasing capsule according to claim 8, wherein said cool-curable polymer is selected from the group consisting of gelatin and agar and said salt-curable polymer is selected from the group consisting of sodium alginate, pectin, carageenan, carboxymethyl cellulose, gelant gum, and synthetic polymers obtained from sodium acrylate and sodium methacrylate.

10. A gradual-releasing capsule according to claim 1, wherein said capsule has a grain size of from about 1 to about 5 mm.

11. A gradual-releasing capsule according to claim 1, wherein said capsule has a breaking strength of from about 100 to about 5,000 g/cm$^2$.

12. A gradual-releasing capsule according to claim 1, wherein said hydrophobic oil is selected from the group consisting of musk oil, ambut seed oil, ylang yalang oil, oakmoss oil, opopanax oil, rose oil, linalool, linalyl acetate, menthol, hedion, lemon terpene, orange terpene, spearmint oil, peppermint oil, lime oil, eugenol, citronellol, musk ketone, and mixtures thereof.

13. A gradual-releasing capsule according to claim 1, wherein said hydrophobic oil is diluted with a diluent in an amount of 100 to 1,000 parts by weight per 100 parts by weight of the hydrophobic oil.

14. A gradual-releasing capsule according to claim 1, wherein the core body contains 1 to 300 parts by weight of the hydrophobic oil for 100 parts by weight of the polymer.

15. A method for manufacturing a gradual-releasing capsule comprising:

dripping a liquid core body-forming composition containing a hydrophobic oil and a reactive monomer and a solution of a natural curable polymer and/or a synthetic curable polymer from a multiple nozzle into a coagulating solution for said curable polymers to form a primary capsule in which a liquid droplet of a core body-forming composition containing said hydrophobic oil and said reactive monomer is coated with a cured product of said natural curable polymer and/or said synthetic curable polymer; and polymerizing the reactive monomer.

16. A method for manufacturing a gradual-releasing capsule according to claim 15, wherein the core body-forming composition further contains a polymerization initiator and/or diluent.

17. A method for manufacturing a gradual-releasing capsule according to claim 16, wherein the core body-forming composition contains a polymerization initiator in an amount of 0.1 to 0.5 parts by weight per 100 parts by weight of the reactive monomer.

18. A method for manufacturing a gradual-releasing capsule according to claim 16, wherein the core body-forming composition contains a diluent for the hydrophobic oil, the amount of the diluent being 100 to 1,000 parts by weight per 100 parts by weight of the hydrophobic oil.

19. A method for manufacturing a gradual-releasing capsule comprising:

dripping a liquid core body-forming composition containing a hydrophobic oil and a reactive monomer and a solution of a natural curable polymer and/or a synthetic curable polymer from a multiple nozzle into a coagulating solution for said curable polymers to form a primary capsule in which a liquid droplet of a core body-forming composition containing said hydrophobic oil and said reactive monomer is coated with a cured product of said natural curable polymer and/or said synthetic curable polymer;

polymerizing the reactive monomer to form a secondary capsule; and introducing the secondary capsule into an aqueous alkali to remove or weaken the shell body.

20. A method for manufacturing a gradual-releasing capsule according to claim 19, wherein the core body-forming composition further contains a polymerization initiator and/or diluent.

21. A method for manufacturing a gradual-releasing capsule according to claim 20, wherein the core body-forming composition contains a polymerization initiator in an amount of 0.1 to 0.5 parts by weight per 100 parts by weight of the reactive monomer.

22. A method for manufacturing a gradual-releasing capsule according to claim 20, wherein the core body-forming composition contains a diluent for the hydrophobic oil, the amount of the diluent being 100 to 1,000 parts by weight per 100 parts by weight of the hydrophobic oil.

* * * * *